(12) United States Patent
Berndt et al.

(10) Patent No.: US 9,970,868 B2
(45) Date of Patent: May 15, 2018

(54) NEPHELOMETRY METHOD AND APPARATUS FOR DETERMINING THE CONCENTRATION OF SUSPENDED PARTICLES IN AN ARRAY OF SAMPLE CONTAINERS

(71) Applicants: Becton, Dickinson and Company, Franklin Lakes, NJ (US); David W. Highet, Teaneck, NJ (US)

(72) Inventors: Klaus W. Berndt, Cockeysville, MD (US); Timothy R. Hansen, Spring Grove, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days. days.

(21) Appl. No.: 14/913,148

(22) PCT Filed: Aug. 19, 2014

(86) PCT No.: PCT/US2014/051645
§ 371 (c)(1),
(2) Date: Feb. 19, 2016

(87) PCT Pub. No.: WO2015/026794
PCT Pub. Date: Feb. 26, 2015

(65) Prior Publication Data
US 2016/0209328 A1   Jul. 21, 2016

Related U.S. Application Data

(60) Provisional application No. 61/868,711, filed on Aug. 22, 2013.

(51) Int. Cl.
*G01N 21/00* (2006.01)
*G01N 21/51* (2006.01)
(Continued)

(52) U.S. Cl.
CPC ............. *G01N 21/51* (2013.01); *G01N 15/06* (2013.01); *G01N 2015/0693* (2013.01);
(Continued)

(58) Field of Classification Search
CPC ........... G01N 21/51; G01N 2015/0693; G01N 21/82; G01N 21/59; G01N 35/00623; G01N 15/065; G01N 21/07
(Continued)

(56) References Cited

U.S. PATENT DOCUMENTS
4,509,856 A   4/1985 Lee
4,685,801 A   8/1987 Minekane
(Continued)

FOREIGN PATENT DOCUMENTS
EP   0950892 A2   10/1999
EP   1632762      3/2006
JP   2000512747 A  9/2000

OTHER PUBLICATIONS
International Search Report and Written Opinion for Application No. PCT/US2014/051645 dated Nov. 21, 2014.

*Primary Examiner* — Isiaka Akanbi
(74) *Attorney, Agent, or Firm* — Botos Churchill IP Law LLP

(57) ABSTRACT

Described are devices, methods, and systems that are suitable for rapidly and simultaneously determining the concentration of suspended particles in a sample. The devices, methods, and systems allow for the rapid and simultaneous interrogation of a large number of sample wells in a single vessel, for example, samples contained in a two-dimensional array or micro-titer plate, without the need for moving reading heads or moving the sample vessel. The nephelometry system allows the user to rapidly and simultaneously measure the concentration of the particles in numerous samples, adjust the concentration of the particles in the sample with a sample handling system, and re-measure the concentration of the samples in order to achieve a desired concentration.

21 Claims, 8 Drawing Sheets

(51) Int. Cl.
*G01N 15/06* (2006.01)
*G01N 21/47* (2006.01)

(52) U.S. Cl.
CPC ........... *G01N 2021/4709* (2013.01); *G01N 2021/4761* (2013.01); *G01N 2021/513* (2013.01); *G01N 2201/0446* (2013.01); *G01N 2201/062* (2013.01)

(58) Field of Classification Search
USPC ............... 356/237.2–237.6, 342, 338, 341
See application file for complete search history.

(56) References Cited

U.S. PATENT DOCUMENTS

| | | | |
|---|---|---|---|
| 5,854,684 A * | 12/1998 | Stabile | G01N 21/253 356/417 |
| 5,872,361 A | 2/1999 | Paoli et al. | |
| 5,969,814 A | 10/1999 | Barber et al. | |
| 6,388,788 B1 * | 5/2002 | Harris | G02B 21/0028 250/234 |
| 8,928,884 B2 * | 1/2015 | Hattori | G01N 21/59 356/128 |
| 2002/0030815 A1 | 3/2002 | Ichijo | |
| 2003/0214653 A1 | 11/2003 | Palumbo et al. | |
| 2004/0156748 A1 * | 8/2004 | Yamakawa | B01L 3/021 422/64 |
| 2006/0120566 A1 | 6/2006 | Myogadani et al. | |
| 2006/0127277 A1 * | 6/2006 | Numajiri | G01N 35/08 422/65 |
| 2006/0166373 A1 * | 7/2006 | Enoki | B01L 3/0241 436/180 |
| 2007/0127027 A1 * | 6/2007 | Kralik | G01N 21/31 356/432 |
| 2010/0272608 A1 * | 10/2010 | Penterman | G01K 11/00 422/69 |
| 2011/0110822 A1 * | 5/2011 | Adachi | G01N 21/253 422/82.09 |

\* cited by examiner

NEPHELOMETRY METHOD AND APPARATUS FOR DETERMINING THE CONCENTRATION OF SUSPENDED PARTICLES IN AN ARRAY OF SAMPLE CONTAINERS

CROSS-REFERENCE TO RELATED APPLICATIONS

The present application is a national phase entry of 35 U.S.C. § 371 of International Application No. PCT/US2014/051645 filed Aug. 19, 2014, published in English, which claims priority from U.S. Provisional Application No. 61/868,711 filed Aug. 22, 2013, all of which are incorporated herein by reference.

BACKGROUND OF THE INVENTION

Nephelometry is a technique used for measuring the concentration of particles suspended in a liquid sample. A conventional nephelometer includes a light source, a sample container, and an optical detector at a predetermined position and orientation (usually 90 degrees) with respect to the light source and the sample being tested. The optical detector produces a relatively low-level analog signal in response to the presence of light-scattering particles suspended in the liquid media, with the back-scatter signal being proportional to the concentration of the particles.

In designing a nephelometer, care has to be taken that no direct light from the source and no stray light originating at surfaces can reach the optical detector. Such light would elevate the background signal, making it impossible to detect very low particle concentrations. U.S. Pat. No. 5,872,361 discloses a nephelometer design whereby a non-imaging concentrator is positioned in-between the light beam and the optical detector, allowing excellent collection of scattered photons, but blocking un-wanted contributions from the device surfaces. U.S. Patent Publication No. 2003/0214653 discloses a nephelometer arrangement of internal surfaces, optical surfaces, and light baffles to the field of view of both the illumination beam and the detector means that significantly improves the lower detection limit by reducing signal contributions due to stray light.

Nephelometry techniques are used in different fields of life sciences, such as, immunology and clinical microbiology, but also in environmental sciences for monitoring air pollution or the clarity of drinking water. The dominant application of nephelometry in clinical microbiology is related to monitoring a microorganism inoculum concentration during sample preparation for microbial growth studies, such as, antimicrobial susceptibility testing ("AST"). The standard method of estimating the concentration of a microorganism in a sample is based on obtaining a quantitative value known as a McFarland value. McFarland standards are known concentrations of microbial solutions that can be used to prepare a standard curve in order to determine the concentration of particles in a sample, such as, e.g., the concentration of bacteria in a positive blood culture sample. In addition, in the clinical lab, there is a need to rapidly and accurately identify and characterize microorganism(s) in a multitude of samples in order to provide appropriate guidance to the physician in a timely manner. These identification and characterization methods often require the determination of the concentration of the microorganism in the sample prior to such testing.

Most nephelometers are equipped with only one illumination and detection path, and can accept only one sample container at a time. For high-throughput applications, including a multitude of sample containers such as a multi-well micro-titer plate, it is very time consuming to measure the concentration of the suspended particles in each sample in serial mode fashion.

Efforts have been made to provide a nephelometer with increased through-put. U.S. Pat. No. 5,969,814 discloses a nephelometer for interrogating a multitude of sample containers that are mounted on a revolving platform or carousel. In order to measure the concentration of suspended particles in a particular sample container, the carousel rotates until that container is aligned with an illumination and detection assembly for sample interrogation.

A nephelometer containing a circularly arranged array of optical cuvettes, mounted on a fast moving rotor assembly, is disclosed in U.S. Pat. No. 4,509,856. In this design, the nephelometric cuvettes themselves pass a location where they are interrogated by two illumination beams. Light emerging from the cuvette at angles of 90° and 180° relative to the illumination beams is measured by an optical detector.

EP Patent No. 0950892 discloses a nephelometer for interrogating an array of liquid sample containers that are arranged in a standard 96-well micro-titer plate format. The disclosed apparatus is equipped with a measuring head equipped with a light source and an optical detector to measure the transmitted light in a single well. The measuring head and the micro-titer plate are then moved in relation to each other, so that the optical density of each sample is measured in serial mode.

U.S. Pat. No. 4,685,801 discloses a multi-channel nephelometer wherein light from a single source is coupled into twelve illumination fibers simultaneously to optically interrogate twelve sample containers. Light transmitted from the sample containers is directed into one of twelve collection fibers. The emission ends of these collection fibers are disposed in a circular arrangement in a support member. The support member is then rotated so that light emitted from these fibers is directed to a photo diode sensor in serial fashion.

The above-described nephelometers fail to provide a device that is capable of determining the concentration of suspended particles in sample without the need for serial mode detection and the complicated mechanical devices needed to effect such detection. Accordingly, there is a need for a nephelometer that is capable of simultaneously determining the concentration of suspended particles in numerous samples. In addition, the nephelometer must be capable of detecting very low particle concentrations. In order to do so, background signal must be minimized. Consequently, improvement in automated, high throughput nephelometers continues to be sought.

BRIEF SUMMARY OF THE INVENTION

Described herein are nephelometry devices, methods, and systems for measuring the concentration of particles suspended in a liquid sample. The devices and methods described herein are suitable for rapidly and simultaneously determining the concentration of suspended particles in a large number of samples, such as, for example, a vessel segmented into individual sample wells such as a micro-titer plate. The devices, methods, and systems described herein allow for the rapid and simultaneous interrogation of a large number of samples without the need for relative movement of the interrogating apparatus or the sample wells.

One aspect of the invention described herein provides for a nephelometry device for measuring the concentration of particles suspended in a liquid sample. The device is configured to receive a vessel segmented into an array of individual sample wells. The wells are optically transmissive and preferably have a flat bottom. The array of wells is positioned over a horizontal opening on the top of a housing. Banks of light sources are positioned within the housing flanking the wells at the opening. The banks extend along the wells, along two sides of the opening. The light sources uniformly illuminate the bottoms of the entire array of sample wells. A photoelectric sensor array is positioned within the housing. The housing also has an imaging system that is oriented to receive light from the light sources that is reflected by the samples in the vessel. The photoelectric sensor array is positioned to detect back-scatter light produced by the particles in each sample upon illumination by the light sources. The photoelectric sensor array is configured such that each sensor or group of sensors will receive back-scatter light that can be attributed to a sample in the vessel.

Another aspect of the invention relates to methods for measuring the concentration of particles suspended in a liquid sample. The methods include providing a vessel segmented into individual sample wells, each well having an optically transmissive, preferably transparent, bottom. The sample wells have liquid samples disposed therein. The samples themselves will be interrogated to determine the presence, absence, and concentration, of suspended particles therein. The well bottoms are preferably flat. All wells are illuminated uniformly and simultaneously. The light is directed to the well bottoms. Preferably, the light is directed onto the well bottoms at an oblique angle of incidence. The light back-scattered from the samples in the wells is collected and measured. A photoelectric sensor array cooperates with an imaging system to detect the light back-scattered by the sample in each well. The imaging system preferably has an axis of symmetry that is oriented essentially perpendicular to the plane formed by the sample well bottoms. Back-scattered light is detected by the photoelectric sensor array which is preferably an array of photodiodes. The array of photodiodes produces a photocurrent. The photocurrent is then processed via software to determine the photocurrent associated with each particular well in the vessel. In turn, each well is associated with a particular sample. In one embodiment the photocurrent from a particular quadrant of the photodiode array is selected wherein the quadrant is correlated with the location of a well (which has a particular sample therein) in the vessel. The concentration of suspended particles in each sample is then determined by comparing the photocurrent associated with a particular sample in a particular well with a photocurrent calibration value determined from a standard curve of known concentration of particles as a function of photocurrent.

Another aspect of the invention relates to nephelometry systems for measuring the concentration of particles suspended in a liquid sample. The systems described herein include an instrument controller in conjunction with the nephelometry device described herein in which an array of sample wells (containing sample) in a vessel are interrogated using stationary light sources and stationary photodetectors. The system further includes a sample handling system having a pipette for introducing or removing sample from the wells in the vessel, an image processor, and a system computer with a display feature. The light sources of the nephelometry device, the handling system, the image processor, and the system computer are connected to and controlled by the instrument controller. The system computer is in communication with the instrument controller, the photoelectric sensor array of the nephelometry device, and the image processor. The nephelometry system described herein allows the user to rapidly and simultaneously measure the concentration of the particles in numerous samples, adjust the concentration of the particles in the sample with the sample handling system, and re-measure the concentration of the samples in order to achieve a desired concentration.

DETAILED DESCRIPTION

Nephelometry Device

Figure 1:
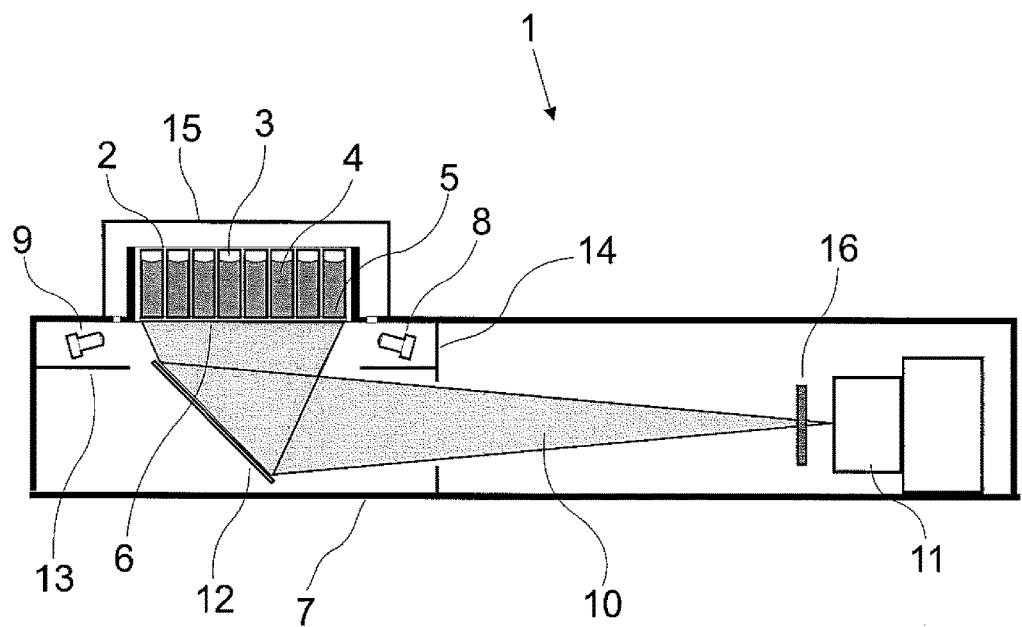
FIG. 1 illustrates one embodiment of an optical configuration of a nephelometer device described herein that contains a 45 degree mirror.

FIG. 1 illustrates one embodiment of the nephelometry device contemplated by the present invention, in which a vessel segmented into an array of individual sample wells is interrogated using stationary light sources and stationary photodetectors. FIG. 1 illustrates nephelometry device 1. A vessel 2 segmented into array of sample wells 3, for example, in the form of a two-dimensional micro-titer plate, is positioned over an opening 6 in the top of an otherwise opaque and light-tight housing 7. In one embodiment, the micro-titer plate is a 96-well micro-titer plate. Regardless of the number of wells 3 in vessel 2, the side walls of the wells are opaque in order to avoid cross-talk between neighboring wells, which is particularly important if low particle concentrations are to be determined. In one embodiment, a standard micro-titer plate without opaque well walls can be used and placed in a tray or sleeve with opaque side walls and a light transmissive bottom. Each well 3 is capable of receiving a liquid sample of measurement. The system will determine the concentration for suspended particles in the sample. Importantly, each well 3 is equipped with an optically transparent flat bottom 5.

In one embodiment, as depicted in FIG. 1, at least two banks of light sources 8 and 9 are positioned adjacent two sides of opening 6. As illustrated in the cutaway view of the apparatus 1 in FIG. 1 the banks of light sources extend beyond the plane of the paper. Thus only one light source for each bank is depicted in FIG. 1 as is only one row of wells 3 in the vessel 2. Light sources 8 and 9 illuminate the vessel with light, such as, for example, visible light, narrow-band light, ultra-violet light, or broad band light. The choice of illumination light is a matter of design choice, known to those skilled in the art, and can vary depending on the particular type of microorganism being tested. Banks of light sources 8 and 9 provide even and simultaneous illumination of the vessel 2. The well bottoms 5, as illustrated, are flat. While flat bottoms are preferred, other bottom configurations are not precluded by the present invention. If a curved bottom is used, conditions may need to be optimized in order to minimize light anomalies due to a lensing effect. Flat bottoms 5 of all sample wells 3 within the vessel 2 are illuminated by light sources 8 and 9. The angle of incidence at which the light strikes the bottom of the wells (not shown) deviates substantially from the angle of normal incidence. In one embodiment, the angle of normal incidence is defined as zero degrees and the preferred angle of incidence of the light sources 8 and 9 is between about 45 degrees and about 85 degrees. Measured from the plane and defined by the well bottoms the angle of incidence is about 5 degrees to about 45 degrees. In another embodiment, both rows of light sources 8 and 9 are oriented so as to produce illumination light at an angle of incidence near 75 degrees from normal. Although not bound to a particular theory, it is believed that by using oblique illumination of the flat bottoms 5 any light reflected or back-scattered from these surfaces of housing 7 or the components therein is blocked from reaching the detector. Therefore, background signal is minimized.

In one embodiment, solid-state light-emitting diodes are used as light sources 8 and 9, such as, for example, light emitting diodes produced by Cree, Inc. (e.g. model XL7090GRN). Light emitting diodes usually emit narrow-band radiation (i.e. approximately 10-50 nm optical bandwidth). If other, more broad-band sources are used, a spectral filter is inserted into the scattered-light collection path, as shown, for example, by spectral filter 16 in FIG. 1. While light emitting diodes (LEDs) are inexpensive and easily obtained light sources for the nephelometer described herein, other light sources such as halogen bulbs or even pulsed or non-pulsed discharge lamps can be utilized.

In one embodiment, as depicted in FIG. 1, the bottoms 5 of vessel 2 are imaged onto a photoelectric sensor array 11 located within housing 7. The sensor array is, for example, an array of CMOS imagers (i.e. a CMOS chip) axis of symmetry of the imaging system is essentially perpendicular to the plane formed by all flat bottoms 5 in vessel 2. Photoelectric sensor array 11 can detect and record back-scatter light produced by the particles for samples 4 in each well 3 upon illumination by light sources 8 and 9. Although not bound by a particular theory, it is believed that if the illumination light is directed onto vessel bottoms 5 at normal incidence, strong specular reflections, i.e., mirrored reflections of the illumination light, would reach photoelectric sensor array 11, making a meaningful nephelometric measurement impossible. By illuminating the vessel bottoms 5 at an oblique angle of incidence any specular reflections are directed sideways. These specular reflections can be trapped, for example, by means of baffles 13 and 14 located under light sources 8 and 9. Such "trapped" reflections do not reach photoelectric sensor array 11.

The illumination light from light sources 8 and 9 is transmitted through the optically transparent vessel bottoms 5 and into liquid sample 4. The light undergoes multiple scattering events when interacting with the suspended particles (if present) in the sample. Due to these multiple scattering events, the scattered light transmitted from the sample vessel is homogenous and diffuse. The photoelectric sensor array 11 therefore receives an almost even photon density 10 for each sample. The photon density as received by photoelectric sensor array 11 does vary depending on the concentration of suspended particles in a particular well 3. Therefore, the particle concentration in the sample of an individual well can be determined based on the pixel intensity and/or photocurrent of the corresponding image for the entire array. Methods for determining the concentration of particles in each sample is described in more detail below.

Figure 8:
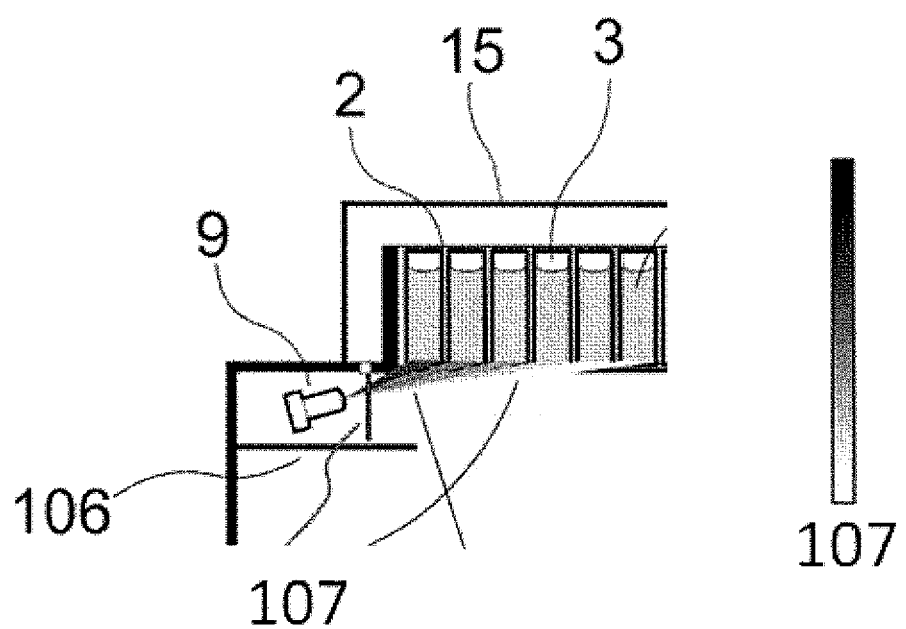
FIG. 8 demonstrates one embodiment in which a gradient neutral density filter is used in front of the light sources.

In one embodiment, in order to ensure that the bottoms of each well 3 are illuminated evenly with illumination light, the incoming photon flux from the illumination light sources 8 and 9 can be equalized before reaching each of the wells. This embodiment, which is depicted in FIG. 8, utilizes a gradient neutral density filter 107 that is added between light sources 8 and 9 and vessel 2. By using gradient neutral density filter 107 each well receives a photon flux during image capture inversely proportional to its square distance from the light source 8 and 9. The gradient neutral density filter 107 allows the system to compensate for any differences in light intensity between wells 3. Commercially available gradient neutral density filters could be used or could be customized for the particular vessel 2 being used. Methods for customizing gradient neutral filters are known to those skilled in the art and are not described in detail herein.

In one embodiment, as depicted in FIG. 1, the photoelectric sensor array 11 is disposed in a digital camera wherein an objective lens is the imaging system. In this embodiment, the photoelectric sensor array (of the digital camera) 11 records the spatial distribution of photon density emitted from the sample in all wells. In one embodiment, the device does not contain a lens but rather contains a photodiode array that is large enough to capture the back-scatter from the entire sample vessel, i.e., the photodiode array is as large as the sample vessel.

In another embodiment, the nephelometry device contains 45-degree mirror 12 that deflects back-scatter light from samples 4 upon illumination of the vessel 2 by light sources 8 and 9. The mirror 12 deflects the back-scattered light to photoelectric sensor array 11. More specifically, mirror 12 redirects the axis of photon density 10 by 90 degrees. This configuration reduces the overall height of the device, and is particularly advantageous, given the need to vertically orient the vessel 2 to ensure that the wells 3 are optimally filled.

In one embodiment, the vessel 2 is covered with an opaque light shield 15. Light shield 15 prevents residual room light from entering the nephelometry device 1. Light shield 15 minimizes background signal from room light. Light shield 15 is particularly useful when interrogating samples with low concentrations of particles.

Figure 3:
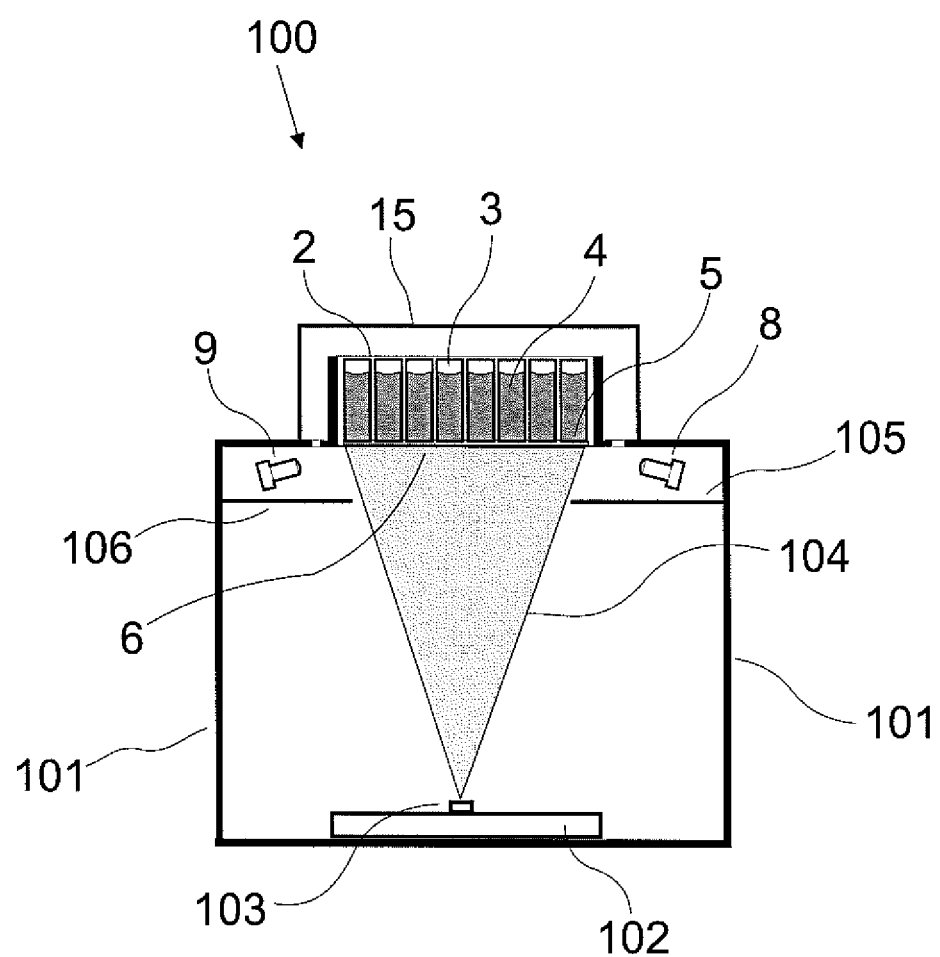
FIG. 3 illustrates one embodiment of an optical configuration of a nephelometer device described herein that does not contain a 45 degree mirror.

FIG. 3 illustrates another embodiment of the nephelometry device 100 described herein. In this embodiment the photoelectric sensor array is disposed in an extremely thin digital camera 102 with small objective lens 103. Any conventional lens known to those skilled in the art may be used. While this embodiment is similar to the embodiment illustrated in FIG. 1, the optical path from the samples to the camera is different. Consequently no 45-degree mirror is required and the alternate housing 101 is significantly smaller.

In another embodiment, when a very small objective lens 103 of a few millimeters diameter is used, the cone of collection 104 provided by the configuration illustrated in FIG. 3 is sufficient for a reliable back-scattering measurement by focusing the back-scatter light onto the sensor. In yet another embodiment, the distance between the plane defined by the well bottoms 5 and the objective lens 103 that is needed to generate images of sufficient sharpness and quality is between about 10 and about 12 centimeters. As in the embodiment illustrated in FIG. 1, baffles 105 and 106 block light back-scattered from device surfaces from being transmitted to the photodetector 103.

Nephelometry Methods

One aspect of the invention includes nephelometry methods utilizing the nephelometry devices described herein. One exemplary nephelometry method for determining the concentration of suspended particles in a vessel segmented into individual sample wells includes optically interrogating a vessel containing wells with flat and transparent bottoms. The wells contain liquid sample, at least some of which have particles suspended therein. In one embodiment, the vessel is a common multi-well micro-titer plate. Preferably the side walls of the wells are opaque (or placed within opaque sleeves) to reduce cross-talk transmission of illumination light between sample wells.

The bottoms of the wells are illuminated evenly and simultaneously. The light for illumination is incident on the bottoms of the wells at an oblique angle. The illuminating light is back-scattered by the particles in the sample. In one embodiment, the illumination light is visible light or narrow-band visible (UVB) light. In yet another embodiment, the center wavelength of the illumination light is selected so that maximum differential resolution relative to the determined particle concentration is obtained for a concentration range of interest. Because each type of particle has a unique shape and size, the illumination light can be optimized by determining the specific wavelength(s) best suited for a particular particle, i.e., a particular species of bacteria. If the particle (or species of bacteria) is unknown, a broad band light source can be used to ensure detection of a wide variety of particle shapes and sizes. In one embodiment, green light with a center wavelength around 525 nm is used as the illumination light.

Next, the well bottoms of the vessel are imaged onto a photoelectric sensor array. The axis of symmetry of the imaging system used to direct light back-scattered from the sample array to the sensor array is oriented essentially perpendicular to the plane defined by bottoms of the wells in the vessel. In one embodiment, the photoelectric sensor array is a CMOS chip. In another embodiment, the imaging system is a digital camera. Depending upon the wavelength(s) of the imaging light a spectral filter can be provided for the sensor array. In yet another embodiment, the imaging system contains a low-profile smart camera.

The light back-scattered from the sample is received by the photoelectric sensor array, which produces a total photocurrent. The total photocurrent is processed via software to determine the photocurrent associated with each sample vessel in the array. This is accomplished by associating a region of the sensor array with light from a particular well by selecting the quadrant or region associated with the well using software and a computer system. The photocurrent intensity for a given sample is then compared with previous images or calibration values from a standard curve. Based on the comparison, a measured pixel intensity or photocurrent associated with a particular well can be used to measure the concentration of particles in the sample by measuring the photocurrent that is produced by the selected quadrant or region of the sensor array. In one embodiment, the sample contains microorganisms suspended in a solution and the standard curve is a collection of samples containing microorganism at known concentrations (i.e. McFarland).

In another embodiment, to reduce background pixel intensity, i.e., noise, the total photocurrent of the photoelectric sensor array is used to calculate the average photocurrent attributed to each well in the vessel. A corrected average photocurrent for all sample wells is then calculated by subtracting the average photocurrents obtained without illumination from the average photocurrents obtained with illumination.

In yet another embodiment the source light is periodically intensity-modulated and the photoelectric sensor array has time-gating capability, so that effective room-light suppression can be accomplished by applying synchronous-detection principles. This method allows for the elimination of background signal from a constantly interfering light source that is smaller in intensity then the illumination source. This method is particularly useful if the user is unable to provide a dark environment while analyzing the samples.

In another embodiment, residual heterogeneities in the scattered light distribution across a vessel can be canceled out by calculating an average pixel intensity and/or an average photocurrent for the quadrant or region of the sensor array associated for each well. By comparing the calculated average photocurrent for each well with average-photocurrent calibration values previously determined the actual concentration of suspended particles in each well can be determined.

In another embodiment, linearity and signal-to-noise ratio (SNR) is calibrated for each well position in the vessel in order to evaluate and report the confidence of the measured intensity for each well. The confidence of the measured light intensity can be increased by capturing a first image of each well, and then capturing additional images of each well. The number of images captured is not limited but can vary depending on the amount of time the user may want to spend on capturing the images or the quality of the image that the user is attempting to achieve; however the confidence value of a given set of captured images is increased as the number of images is taken. Therefore, the user may want to increase the number of images captured in order to achieve a given confidence value. In another embodiment, the user can achieve a signal intensity that maximizes the signal-to-noise ratio without saturation of the signal intensity. Optimally, the signal intensity is just below saturation. This can be achieved, for example, by capturing a first image of the vessel. If the exposure time used to capture the first image of the vessel has not reached saturation, a subsequent image can be captured increasing the exposure time. Additional subsequent images can be captured until maximum intensity is achieved without saturation of the signal in order to maximize the signal-to-noise ratio.

In one embodiment, the capture of the pixel intensity from the back-scatter light is a "snapshot" of intensity at any given time. In another embodiment, the device is designed to perform a continuous reading of the back-scatter light across a period of time selected by the user.

Nephelometry System

Figure 2:
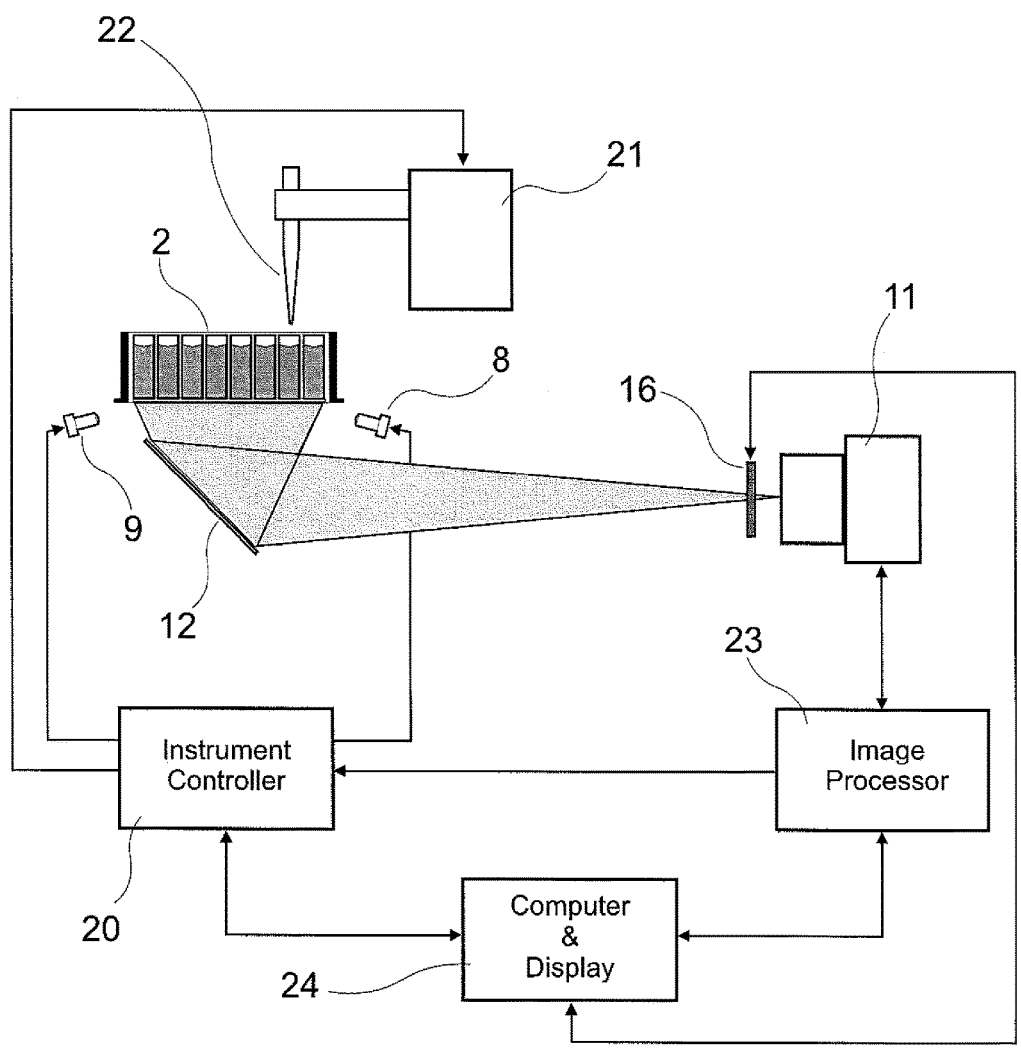
FIG. 2 illustrates one embodiment of a nephelometer system described herein.

FIG. 2 is a diagram of one embodiment of a nephelometer system comprising any of the nephelometry devices described herein for determining the concentration of suspended particles in a vessel segmented into individual sample wells. As depicted in FIG. 2, the nephelometry system may include instrument controller 20; sample handling system 21 including an automatic pipette 22; image processor 23; and system computer 24 with a display feature. Any of the nephelometry devices described herein can be used in this system but the device of FIG. 1 is illustrated. In one embodiment, light sources 8 and 9 of the nephelometry device, handling system 21, image processor 23, and system computer are connected to instrument controller 20. In another embodiment, system computer 24 is in communication with instrument controller 20, photoelectric sensor array 11 of the nephelometry device, and image processor 23.

In one embodiment, system computer 24, responding to a request by the user, activates instrument controller 20 so that sample handling system 21 fills the wells within vessel 2 with liquid sample containing suspended particles. Instrument controller 20 turns on rows of illumination sources 8 and 9. Subsequently, image processor 23 activates photoelectric sensor array 11 containing, for example, a digital camera, to acquire a first image. Image processor 23 then compares the pixel intensities of the newly acquired first image with pixel intensities of a standard image acquired earlier and stored within processor 23. In one example, if there is reasonable agreement in the intensity levels between the two images, image processor 23 shifts instrument controller 20 into its default starting status, which includes turning sources 8 and 9 off. The newly acquired first image is then sent from processor 23 to computer 24 for analysis relative to the particle concentration in the individual sample containers within vessel 2. If rows of illumination sources 8 and 9 represent broad-band sources, the user has an option to select a particular spectral emission window via computer 24 and spectral filter 16, which can be a tunable filter.

In another embodiment, the nephelometry system for determining the concentration of suspended particles in an array of sample containers contains a nephelometry device for determining the concentration of suspended particles in a vessel segmented into individual sample wells. The nephelometry device contains: a vessel segmented into a plurality of sample wells positioned on a housing over an opening in the housing, wherein each sample well is capable of receiving a liquid sample and wherein the plurality of sample wells have a bottom that is optically transmissive; a plurality of light sources positioned within the housing, flanking the wells, wherein the light sources uniformly illuminate the bottoms of the plurality of sample wells; and a photoelectric sensor array positioned within the housing containing an imaging system that is oriented to receive back-scatter light produced by particles, if present, in each sample upon illumination by the light sources, and wherein the photoelectric sensor array is configured such that each sensor or group of sensors will receive back-scatter light that is associated with at least one well in the array. The nephelometry system also contains a sample handling system comprising a robotic pipette adapted to introduce sample into sample wells of the vessel in response to instructions from an instrument controller. An image processor for receiving an image the illuminated bottom of the vessel is disposed on the nephelometry device housing. In addition, a system computer adapted to receive instructions from an operator and, in response thereto, provide instructions to the instrument controller and the image processor, obtain the image of the illuminated bottom of the vessel, and based upon the image, determine a concentration of particles in at least one sample in at least one well of the vessel.

The nephelometric system shown in FIG. 2 can also be used, for example, in an extended mode of operation. In this embodiment, after determining the particle concentration in each individual sample container, deviations from particular target concentrations can be corrected by activating sample handling system 21 via system computer 24 and instrument controller 20 so that the existing particle concentration is adjusted by adding sample liquid of higher particle concentration, or adding sample liquid containing no particles, as needed. Verification of the corrective measures can then be performed by repeating the procedure described herein for determining the concentration of the particles in the sample. This extended mode of operation may be of particular interest when made part of a Totally Automated Laboratory ("TLA") system. In a TLA system, vessel could rest on a conveyor belt (not shown in FIG. 2) allowing transport of vessel 2 into and out of the nephelometric concentration-measuring/adjustment station described herein.

Example 1

Five samples containing known concentrations of microorganism were prepared for use as a standard curve at 4.0, 3.0, 2.2, 1.2, and 0.5 McFarland. The samples were recorded with the nephelometer described herein with a narrow-band illumination source near 525 nm (green). The diameter of the flat vessels bottoms containing these samples was 16 mm, and the vessels were only partially filled with liquid sample. The samples containers were positioned at an oblique angle relative to a horizontal line to make sure that at least a liquid column of approximately 20 mm was present near the inner bottom walls.

Figure 4:
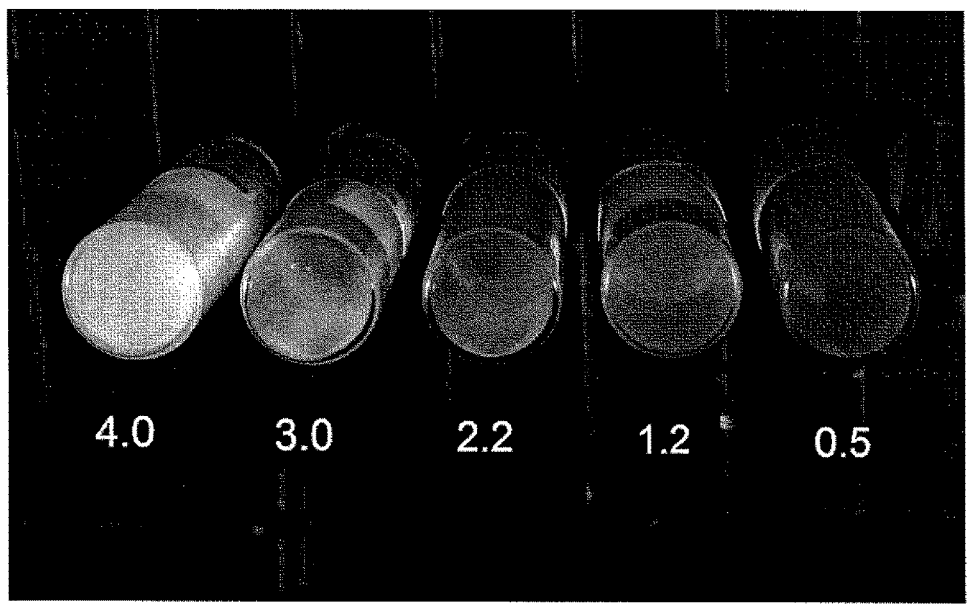
FIG. 4 is an image of five containers with samples at concentrations of 4.0, 3.0, 2.2, 1.2, and 0.5 McFarland recorded with the nephelometer and methods described herein in which the sample containers were positioned at an oblique angle relative to a horizontal line.
Figure 5:
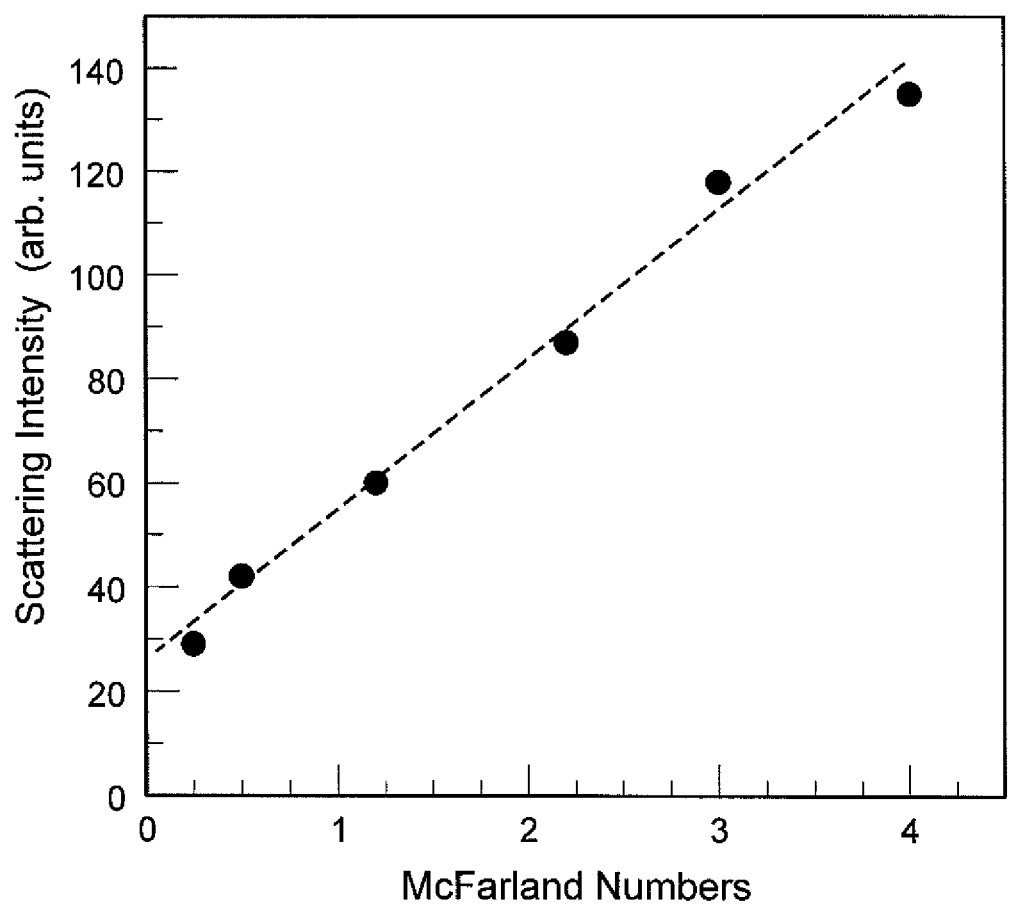
FIG. 5 demonstrates a graph displaying the intensity of the back-scattered light versus the McFarland number for the image of FIG. 4.

FIG. 4 shows an image of the five sample containers recorded on the nephelometer. The light intensity values versus the McFarland number was plotted on a graph (FIG. 5). The results indicate that a good differential resolution is achieved for McFarland numbers between 1.0 and 4.0 using green 525 nm illumination light. The results also demonstrate that the methods, devices, and systems described herein provide superior sensitivity and linearity across a wide range of concentrations.

Example 2

Figure 6:
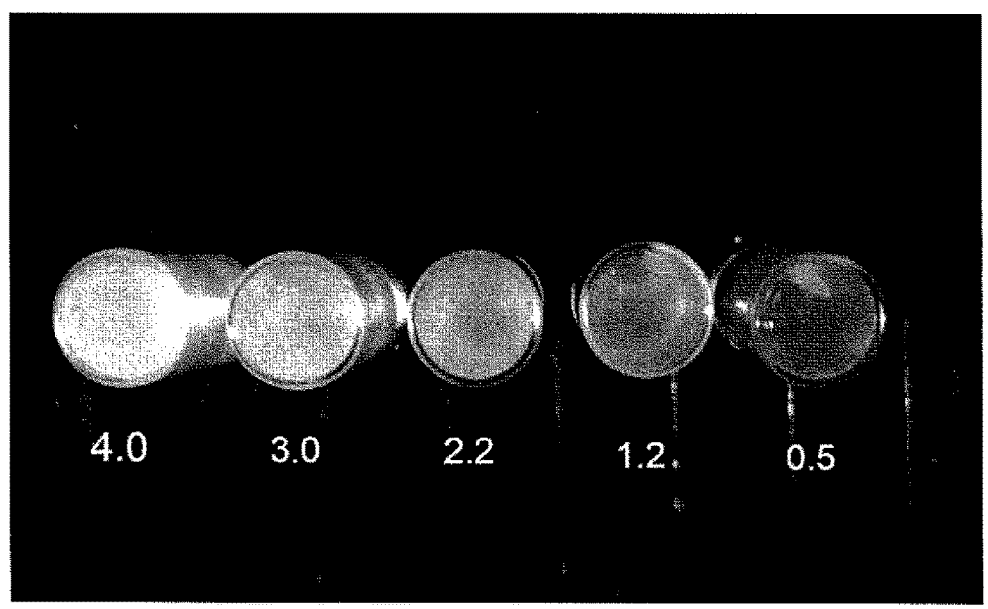
FIG. 6 is an image of five containers with samples at concentrations of 4.0, 3.0, 2.2, 1.2, and 0.5 McFarland recorded with the nephelometer and methods described herein in which the sample containers were positioned at a vertical position.
Figure 7:
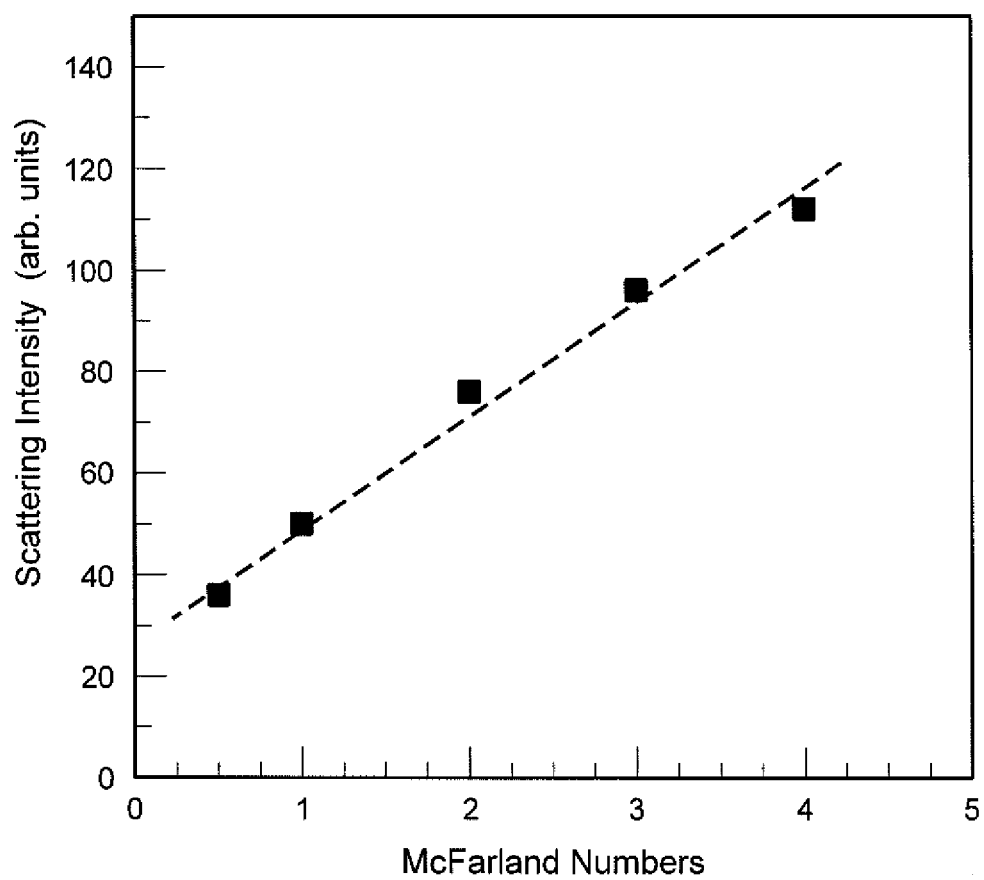
FIG. 7 demonstrates a graph displaying the intensity of the back-scattered light versus the McFarland number for the image of FIG. 6.

A similar method was performed as in Example 1 except that the sample containers were close to a perfect vertical orientation, which resulted in a more homogeneous back-scattered light distribution (FIG. 6). The light intensity values versus the McFarland number was plotted on a graph (FIG. 7). As with Example 1, the results indicate a good differential resolution and superior sensitivity and linearity across a wide range of concentrations.

While different embodiments of the invention have been disclosed and described in detail herein, it may be apparent to those skilled in the art that various changes in form and detail may be made therein without departing from the spirit and scope thereof.

The invention claimed is:

1. A nephelometry system for determining the concentration of suspended particles in an array of sample containers comprising:
   a) nephelometry device for determining the concentration of suspended particles, in a vessel segmented into individual sample wells comprising:
      a vessel segmented into a plurality of sample wells positioned on a housing over an opening in the housing, wherein each sample well is capable of receiving a liquid sample and wherein the plurality of sample wells have a bottom that is optically transmissive;

a plurality of light sources positioned within the housing, flanking the sample wells, wherein the light sources uniformly illuminate the bottoms of the plurality of sample wells; and a photoelectric sensor array positioned within the housing containing an imaging system that is oriented to receive back-scatter light produced by particles, if present, in each sample upon illumination by the light sources, and wherein the photoelectric sensor array is configured such that each sensor or group of sensors will receive back-scatter light that is associated with at least one well in the array;

b) a sample handling system, comprising a robotic pipette adapted to introduce sample into the sample wells of the vessel in response to instructions from an instrument controller;

c) an image processor for receiving an image of the illuminated bottom of the vessel disposed on the nephelometry device housing; and d) a system computer adapted to receive instructions from an operator and, in response thereto provide instructions to the instrument controller and the image processor, obtain the image of the illuminated bottom of the vessel, and based upon the image, determine a concentration of particles in at least one sample in at least one well of the vessel.

2. The system of claim 1, wherein the housing is opaque and light-tight.

3. The system of claim 1, wherein the vessel is a multi-well micro-titer plate.

4. The system of claim 1, wherein the sample wells have flat bottoms.

5. The system of claim 1, wherein the light sources illuminate the bottoms of the sample wells with light selected from the group consisting of visible light, narrow-band light, ultra-violet light, and broad band light.

6. The system of claim 1, wherein the light sources are light-emitting diodes.

7. The system of claim 1, wherein walls of the sample wells are opaque.

8. The system of claim 1, further comprising baffles located under the light sources, wherein the baffles are configured to trap specular reflections and prevent those specular reflections from reaching the photoelectric sensor array.

9. The system of claim 1, wherein the photoelectric sensor array comprises a CMOS chip.

10. The system of claim 1, wherein the photoelectric sensor array comprises a digital camera.

11. The system of claim 10, wherein the digital camera comprises an objective lens that transmits the back-scattered light to the photoelectric sensor array.

12. The system of claim 1, further comprising a 45 degree mirror that deflects back-scatter light to the photoelectric sensor array.

13. The system of claim 1 further comprising a gradient neutral filter interposed between each light source and the vessel.

14. The system of claim 1, wherein the vessel is covered with an opaque light shield at the opening of the housing.

15. The system of claim 1, wherein each well has a flat and optically transmissive bottom.

16. The system of claim 1, wherein the vessel is a multi-well, micro-titer plate.

17. The system of claim 1, wherein the light sources illuminate the bottoms of all sample wells with visible light.

18. The system of claim 1, wherein the light sources illuminate the bottoms of all sample wells with narrow-band light.

19. The system of claim 1, wherein the bottoms of the sample wells are illuminated by the light sources at an angle of incidence that deviates from a normal angle of incidence by 45 degrees to 85 degrees.

20. The system of claim 1, wherein the bottoms of the sample wells are illuminated by the light sources at an angle of incidence that deviates from a normal angle of incidence by 75 degrees.

21. The system of claim 1, wherein the instrument controller determines that the particle concentration of the sample is outside a preset range of particle concentrations, the instrument controller instructs the robotic pipette add liquid sample without particle if the concentration is above the preset range and to concentrate the particle in the sample if the particle concentration is below the preset range.

* * * * *